(12) United States Patent
Liao

(10) Patent No.: US 7,314,641 B1
(45) Date of Patent: Jan. 1, 2008

(54) HIGH-BIOAVAILABILITY PARTICLE COATED WITH FUNGICIDE AND POLYMER

(75) Inventor: Ta-Ping Liao, Chia Yi (TW)

(73) Assignee: Everest Pharm. Industrial Co., Ltd., Chia Yi Hsie (TW)

( * ) Notice: Subject to any disclaimer, the term of this patent is extended or adjusted under 35 U.S.C. 154(b) by 0 days.

(21) Appl. No.: 11/785,438

(22) Filed: Apr. 18, 2007

(51) Int. Cl.
| *A61K 9/16* | (2006.01) |
| *A61K 9/00* | (2006.01) |
| *A61K 9/24* | (2006.01) |
| *A61K 9/14* | (2006.01) |

(52) U.S. Cl. ...................... 424/490; 424/400; 424/472; 424/489

(58) Field of Classification Search ................ 424/490, 424/400, 472, 489
See application file for complete search history.

(56) References Cited

U.S. PATENT DOCUMENTS 6,673,373 B2 * 1/2004 Lee et al. ................... 424/490

FOREIGN PATENT DOCUMENTS

TW            376322         12/1999

* cited by examiner

*Primary Examiner*—Michael G. Hartley
*Assistant Examiner*—Paul W Dickinson
(74) *Attorney, Agent, or Firm*—Rosenberg, Klein & Lee

(57) ABSTRACT

The present invention discloses a high-bioavailability particle coated with fungicide and polymer, which mainly comprises: (a) a coating layer including fungicide, a polymer, an acidic substance, talc, a bonding agent, ethanol and dichloromethane; (b) an anticoagulant layer including talc, hydroxypropyl methylcellulose (HPMC) and a plasticizer; and (c) a particulate core having a diameter ranging from 300 μm to 500 μm (30~50 mesh). In the present invention, the talc is added to prevent the particulate cores from aggregating. In addition, the particulate cores are small-sized enough and the polymer and the acidic substance are added to the coating layer, so that solubility is increased and bioavailability is thus improved.

6 Claims, 1 Drawing Sheet

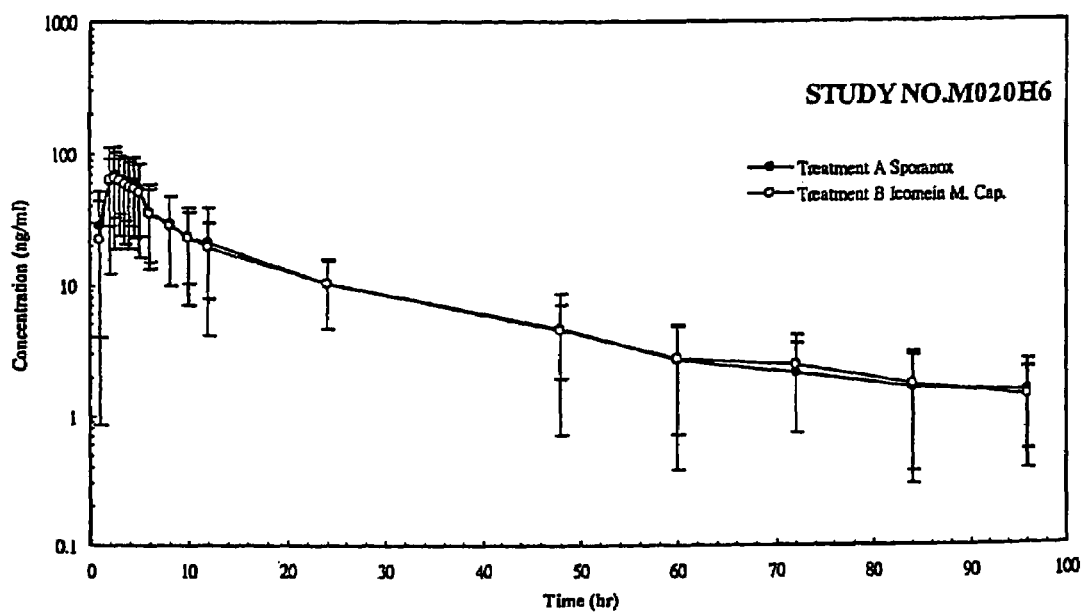

HIGH-BIOAVAILABILITY PARTICLE COATED WITH FUNGICIDE AND POLYMER

BACKGROUND OF THE INVENTION

1. Field of the Invention

The present invention relates to a high-bioavailability particle coated with fungicide and a polymer, which particularly performs high solubility and bioavailability as the particulate cores are small-sized enough.

2. Related Prior Arts

Itraconazole or (+)-cis-4-[4-[4-[-4[[2-(2,4-dichlorophenyl)-2-(1H-1,2,4-triazol-1-ylmethyl)-1,3-dioxolan-4-yl]methoxy]phenyl]-1-piperazinyl]phenyl-2,4-dihydro-2-1(1-methylpropyl)-3H-1,2,4-triazol-3-one is an oral fungicide which is non-enteric application and locally used as disclosed in U.S. Pat. No. 4,267,179.

However, the compound of U.S. Pat. No. 4,267,179 includes itraconazole which is not water soluble, and thus the bioavailability is unsatisfying. The modified itraconazole compound is easily affected by food and pH value of stomach acid, and therefore effect thereof depends on individuals. The itraconazole performs better solubility at pH<2.0, which does not facilitate solubility in human beings.

To solve the above problem, Taiwan Patent No. 376322 provided "a pellet coated with fungicide and polymer", which includes: a) a round or spherical core; b) a coating layer including a hydrophilic polymer selected from the group consisting of hydroxypropyl methylcellulose (HPMC), methacrylate, hydroxypropyl cellulose and polyvidone, an a fungicide selected from the group consisting of itraconazole and saperconazole; and c) a closed coating polymer layer of polyethylene glycol. This pellet is characterized in that the core has a diameter ranging from 600 μm to 700 μm (25~30 mesh); whereby solubility thereof in human beings for treating fungous infection can be promoted.

Unfortunately, though the above pellet coated with fungicide and the polymer can achieve treating effect as expected, aggregation occurs during application because of the too small cores, for example, 30~35 mesh. The minimum sizes of the cores are therefore limited to 25~30 mesh, and solubility in human beings is limited, too. As a result, effect of the treatment is still unsatisfying.

SUMMARY OF THE INVENTION

The present invention discloses a high-bioavailability particle coated with fungicide and polymer. Each particle includes a core on which a coating layer and a packaging layer containing drugs cover. As numerous particles will be dispersed in stomach after being oral application, the area and effect for absorption are wide and improved. The particle of the present invention includes:

(a) a coating layer comprising 20~40 wt. % of itraconazole, 17~30 wt. % of poloxamer 407 polymer, 2~10 wt. % of acidic substance, 15~30 wt. % of talc, 2~6 wt. % of bonding agent, ethanol and dichloromethane based on the coating layer;

(b) an anticoagulant layer comprising 50~70 wt. % of talc, 25~35 wt. % of hydroxypropyl methylcellulose (HPMC) and 1~10 wt. % of plasticizer based on the anticoagulant layer; and (c) a particulate core having a diameter 300~500 μm(30~50 mesh).

By adding the talc during preparation, the fine particulate cores would not aggregate as a bulk. In addition, the particulate cores are small-sized enough and the polymer and the acidic substance are added to the coating layer, so that solubility is increased and bioavailability is thus improved.

In general, the high-bioavailability particle coated with fungicide and polymer comprises 40~60 wt. % of the coating layer, preferably about 51.37 wt. %; 1~10 wt. % of the anticoagulant layer, preferably about 4.51 wt. %; and 34~50 wt. % of the particulate core, preferably about 44.12 wt. %.

BRIEF DESCRIPTION OF THE DRAWINGS

The FIGURE shows average concentrations of itraconazole in bloods sampled from the volunteers taking medicine of the present invention and the traditional medicine.

DETAILED DESCRIPTION OF THE PREFERRED EMBODIMENTS

The present invention mainly includes:

(a) a coating layer including itraconazole, a poloxamer 407 polymer, an acidic substance, talc, a bonding agent, ethanol and dichloromethane;

(b) an anticoagulant layer including talc, hydroxypropyl methylcellulose (HPMC) and a plasticizer; and (c) a particulate core having a diameter ranging from 300 μm to 500 μm (30~50 mesh).

In the above, the anticoagulant layer is used for preventing the cores coating with drugs from aggregation and side effects which will decrease solubility and bioavailability thereof in human beings. In the present invention, content of the talc in the anticoagulant layer preferably ranges 50~70 wt. %. The talc with properties of lubrication and anti-stickiness is suitable for embedding the coating layer therein.

According to the present invention, the core serving as a base can be made by any pharmaceutically acceptable material with a suitable size (30~50 mesh) and hardness. Examples of such material include polymers such as plastic resin; inorganic compounds such as silica gel, glass, hydroxyapatite (sodium chloride or potassium chloride, calcium carbonate or magnesium carbonate) and the like; organic compounds such as active carbon, acids (citrate, fumaric acid, tartaric acid, ascorbic acid, and the like), saccharide and derivatives thereof. The preferred material is saccharide includes sucrose, olygosaccharide, polysaccharide and derivatives thereof, for example, glucose, rhamnose, galactose, lactose, sucrose, mannitol, glucitol, dextrin, maltodextrin, cellulose, carbonylmethylcellulose, starch (corn, tomato, wheat, tapioca), and the like.

In the preferred embodiments of the present invention, 30~50 mesh aspartame (nf xvii, P1989) is used as the cores, which contain 67.5~91.5 wt. % of sucrose and the other can be drug-inert saccharide or dextrin.

Preferably, the particle includes:

(a) a coating layer in a concentration 40~60 wt. %, preferably about 51.37 wt. %, and composed of (1) 20~40 wt. % of itraconazole, (2) 17~30 wt. % of poloxamer 407 polymer, (3) 2~10 wt. % of acidic substance (for example, citric acid, malic acid, acetic acid, etc.), wherein citric acid is more preferred, (4) 15~30 wt. % of talc, (5) 2~6 wt. % of bonding agent (for example, hydroxypropyl methylcellulose (HPMC)), (6) ethanol and (7) dichloromethane based on the coating layer;

(b) an anticoagulant layer in a concentration 1~10 wt. %, preferably about 4.51 wt. %, and composed of (1) 50~70 wt. % of talc, (2) 25~35 wt. % of hydroxypropyl methylcellulose (HPMC), (3) 1~10 wt. % of plasticizer (for example, propylene glycol) based on the anticoagulant layer; and (c) a particulate core in a concentration 34~50 wt. %, preferably about 44.12 wt. %, and having a diameter 300~500 μm(30~50 mesh).

In addition, the particle may further includes additives, for example, thickener, lubricant, surfactant, preservative, complex/chelator, electrolyte and other active compounds such as fire controller, bactericide, disinfectant or vitamin.

These particles can be manufactured as any suitable types in which effective dosage of the fungicide is contained. Preferably, the particles are packed into hard animal capsules each of which includes 50~100 mg of active components. For example, a No. 0 capsule is suitable for encapsulating the particles containing 19~25 wt. % of itraconazole or saperconazole, i.e., about 100 mg of active components.

The particles of the present invention can be conveniently combined with drugs. A coating solution includes a solvent system in which the fungicide, the polymer and the acidic substance are dissolved. The solvent system is a mixture of dichloromethane and alcohol, preferably ethanol. Ethanol can further mixed with methyl ethyl ketone to modify its property. The mixture includes at least 50 wt. % of dichloromethane and at least of 10 wt. 5 of alcohol as hydroxypropyl methylcellulose (HPMC) is insoluble in dichloromethane. Preferably, weight ratio of dichloromethane/ alcohol ranges from 80/20 to 55/45, more preferably about 60/40. Solid content, for example, fungicide and polymer, is preferably ranges from 4 wt. % to 7 wt. %, more preferably about 6 wt. %.

For the cores of 30~50 mesh, coating can be completed in a rotary-spraying granulator.

The spraying speed should be carefully controlled, as spraying too slowly will result in drying of the coating solution and loss of product, and spraying to fast will result in serious bulking up. Therefore, a more slowly initial speed is recommended, and then the speed is increased when the particles "grow up".

During the coating process, pressure of atomized air is also controlled, a lower pressure will result in bigger particles and tend to aggregation, and higher pressure could result in drying of the solution. However, the problem from the high pressure is not critical, and therefore the pressure is almost set to the maximum.

The air flowing rate can be controlled with an outlet valve and optimized according to circulation of the particles. A lower flowing rate will reduce amount of the pellets; and a higher rate may hinder the particles circulating. In the preferred embodiments, the valve is adjusted to about 50 wt. % of the maximum at beginning and then gradually to about 60 wt. %.

During the coating process, temperature of the introduced air is about 40° C.~50° C., and rotary speed of the disk is about 60~80 rpm. A higher temperature may accelerate reaction, but the solvent will evaporate too fast to be uniformly coated on the particles. Consequently, the coating layer is porous, and the solubility of the drugs may reduce to an unacceptable level when the large-sized particles increase. It's apparent that the optimal temperature also relates to equipment, characteristics of the core and the fungicide, batch volume, solvents and spraying speed.

Operation conditions for the coating process will be described in the preferred embodiments, in which reproducibility is also satisfying.

The anticoagulant polymer dissolved in a solvent system is also coated on the cores in a rotary spraying fluidized bed granulator. The solvent system can be, for example, a mixture of dichlormethane and alcohol, preferably ethanol. Ethanol can be further mixed with methyl ethyl ketone to modify its property. Preferably, weight ratio of dichloromethane/alcohol ranges from 80/20 to 55/45, and more preferably about 60/40. In an anticoagulant spraying solution, content of the anticoagulant polymer preferably ranges from 4 wt. % to 7 wt. %, and more preferably about 6 wt. %. This anticoagulant spraying solution facilitates mixing. Operation conditions for this process will be described in the preferred embodiments.

After coating the anticoagulant polymer, a drying procedure for removing excess solvents is required, which takes about 5~15 minutes in the equipment.

Both of the processes for coating drugs and the anticoagulant polymer are preferably carried out in an inert gas. The coating equipment is preferably located on earth, and a concentration system for recycling the solvents is recommended.

The particles coated with drugs can be encapsulated into hard capsules (No. 0) by a standard automatic machine. A coverage and a deionizer may effectively avoid static electrons.

Speed of encapsulating may affect weight distribution. In some preferred embodiments, the speed is controlled at 75%-85% of the maximum speed.

According to the above operation conditions, a particle having a 30~50 mesh core, a coating layer containing the fungicide and polymer and a packaging polymer layer can be produced in simple and good-reproduction processes. Pharmaceutical dynamics also shows the particles have good solubility and bioavailability.

EXAMPLES

A) Preparing the Coating Solution Containing Itraconazole

In a proper container, dichloromethane (337.5 kg) and ethanol (180 kg) are mixed, then poloxamer 407 (22.5 kg) and citric acid (3 kg) are dissolved, then itraconazole (30 kg) and hydroxypropyl methylcellulose (HPMC) (3 kg) are dissolved, and then talc (20.1 kg) is added. The mixture is screened through 100 mesh.

B) Preparing the Coating Solution Containing the Anticoagulant

In a proper container, dichloromethane (15 kg) and ethanol (15 kg) are mixed, hydroxypropyl methylcellulose (HPMC) (2.1 kg) and propylene glycol (300 g) are then dissolved, and then talc (4.5 kg) is added. The mixture is screen through 100 mesh.

c) Loading Drugs

In a rotating granulator equipped with a disk of 1 m diameter, aspartame cores (70.5 kg; 30~50 mesh, 300~500 μm) are placed. Temperature and flowing rate of the inlet gas is about 40° C.~50° C. and about 30~35 m$^3$/min, flowing rate of the outlet gas is about 38 m$^3$/min, rotary speed of the disk is about 60~80 rpm, pressure of the injector is about 3.5~4.5 kg/cm$^2$, and the loading is gradually increased from 450 g/min to 800 g/min. After complete loading, the particles are dried with 50~55° C. air for 20 minutes.

D) Coating the Outer Layer

The dried particles are continued coated. Temperature of the inlet gas is about 50~55° C. Flowing rates of the inlet and outlet gas are remained. Rotary speed of the disk is about 80~90 rpm. Pressure of the injector is about 4.5 kg/cm$^2$. The loading is about 600~700 g/min.

e) Drying

After complete the coating process and stop spraying, rotary speed of the disk is reduced to 10 rpm, temperature of the inlet gas is increased to 55~60° C. for 30 minutes for drying the particles. The particles are then cooled to about 25° C. and discharged into a proper container.

f) Screening

The particles are screened with a multiple sieve of 16 mesh and 30 mesh. The particles are classified into "no good" (over 16 mesh), "good" (16~30 mesh), and "no good" (below 30 mesh).

g) Encapsulating

The "good" particles are encapsulated into No. 0 capsules by an automatic machine. Each capsule contains about 520 mg of particles, i.e., about 100 mg of itraconazole.

As the above capsules containing itraconazole perform good solubility, bioavailability thereof is greatly improved.

Clinic Experiments:

1. Metabolic period of itraconazole in human beings is 96 hours. Contents of itraconazole in medicine of the present invention (Icomein M.) and the traditional medicine (Sporanox) are the same, 100 mg.

2. 24 healthy volunteers are orally applied, and their bloods are sampled after 1, 2, 2.5, 3, 3.5, 4, 4.5, 5, 6, 8, 10, 12, 24, 48, 60, 72, 84 and 96 hours for analyzing contents of itraconazole. For the volunteers taking the traditional medicine, areas under $AUC_{0 \rightarrow t}$ curves are listed in Table 1 and the variant is 60.3.

Table 1 lists the absorption values of 24 volunteers taking the traditional composition Sporanox. Table 2 lists the absorption values of 24 volunteers taking the traditional composition Icomein M. Table 3 lists ratios of areas under concentration-in-blood curves for the present invention to those for the traditional composition.

TABLE 1

| Subject No. | $AUC_{0 \rightarrow t}$ (hr × ng/mL) | $AUC_{0 \rightarrow \infty}$ (hr × ng/mL) | $AUC_{0 \rightarrow t}/AUC_{0 \rightarrow \infty}$ (%) | $C_{max}$ (ng/mL) | MRT (hr) | $T_{max}$ (hr) | $T_{½}$ (hr) |
|---|---|---|---|---|---|---|---|
| 1 | 708 | 735 | 96.3 | 68.0 | 23.6 | 2.00 | 21.5 |
| 2 | 575 | 622 | 92.5 | 60.1 | 30.0 | 5.00 | 34.1 |
| 3 | 1042 | 1113 | 93.7 | 94.4 | 27.2 | 2.50 | 31.0 |
| 4 | 1159 | 1266 | 91.5 | 94.4 | 27.2 | 25.0 | 35.3 |
| 5 | 642 | 673 | 95.3 | 50.0 | 26.6 | 2.00 | 24.8 |
| 6 | 663 | 700 | 94.7 | 52.5 | 28.4 | 2.50 | 25.2 |
| 7 | 808 | 827 | 97.6 | 78.3 | 18.3 | 2.50 | 20.3 |
| 8 | 1199 | 1243 | 96.5 | 115 | 21.2 | 4.0 | 26.7 |
| 9 | 1247 | 1285 | 97.1 | 100 | 21.8 | 3.00 | 25.4 |
| 10 | 652 | 669 | 97.5 | 49.9 | 21.2 | 2.00 | 18.7 |
| 11 | 1205 | 1277 | 94.3 | 124 | 24.6 | 4.50 | 30.8 |
| 12 | 752 | 792 | 95.0 | 83.8 | 22.2 | 2.00 | 31.7 |
| 13 | 868 | 912 | 95.2 | 84.5 | 23.6 | 1.00 | 28.0 |
| 14 | 361 | 396 | 91.2 | 24.4 | 35.1 | 2.00 | 28.5 |
| 15 | 666 | 686 | 97.1 | 67.2 | 22.3 | 2.50 | 21.9 |
| 16 | 750 | 759 | 98.8 | 72.5 | 13.9 | 3.00 | 9.99 |
| 17 | 1654 | 1703 | 97.1 | 123 | 24.7 | 3.50 | 22.0 |
| 18 | 309 | 343 | 90.1 | 17.0 | 34.1 | 4.00 | 30.1 |
| 19 | 2984 | 3227 | 92.5 | 170 | 31.8 | 2.50 | 31.4 |
| 20 | 658 | 670 | 98.2 | 57.6 | 18.0 | 3.00 | 16.2 |
| 21 | 1248 | 1453 | 85.9 | 87.6 | 42.8 | 4.50 | 44.3 |

TABLE 1-continued

| Subject No. | $AUC_{0 \rightarrow t}$ (hr × ng/mL) | $AUC_{0 \rightarrow \infty}$ (hr × ng/mL) | $AUC_{0 \rightarrow t}/AUC_{0 \rightarrow \infty}$ (%) | $C_{max}$ (ng/mL) | MRT (hr) | $T_{max}$ (hr) | $T_{½}$ (hr) |
|---|---|---|---|---|---|---|---|
| 22 | 583 | 629 | 92.6 | 45.5 | 30.2 | 2.00 | 26.8 |
| 23 | 1047 | 1094 | 95.7 | 128 | 22.4 | 2.00 | 25.5 |
| 24 | 277 | 292 | 94.9 | 20.7 | 20.4 | 3.50 | 18.5 |
| Mean | 919 | 974 | 94.6 | 77.9 | 25.6 | 2.83 | 26.2 |
| SD | 554 | 599 | 3.0 | 37.2 | 6.4 | 1.00 | 7.1 |
| CV | 60.3 | 61.5 | 3.17 | 47.8 | 25.0 | 35.2 | 27.3 |

AUC: Area Under the concentration-in-blood curve
$C_{max}$: Concentration max
$T_{max}$: Time of the concentration max
MRT: Mean Residence Time
$T_{½}$: Half-time of the concentration max For the volunteers taking the medicine of the present invention, areas under $AUC_{0 \rightarrow t}$ curves are listed in Table 2 and the variant is 57.9.

TABLE 2

| Subject No. | $AUC_{0 \rightarrow t}$ (hr × ng/mL) | $AUC_{0 \rightarrow \infty}$ (hr × ng/mL) | $AUC_{0 \rightarrow t}/AUC_{0 \rightarrow \infty}$ (%) | $C_{max}$ (ng/mL) | MRT (hr) | $T_{max}$ (hr) | $T_{½}$ (hr) |
|---|---|---|---|---|---|---|---|
| 1 | 1134 | 1196 | 94.8 | 122 | 24.3 | 2.00 | 26.3 |
| 2 | 1190 | 1239 | 96.1 | 110 | 27.8 | 2.00 | 22.9 |
| 3 | 364 | 389 | 93.7 | 26.0 | 24.1 | 2.50 | 19.7 |
| 4 | 993 | 1110 | 89.5 | 97.9 | 35.7 | 2.00 | 37.1 |
| 5 | 1522 | 1552 | 98.1 | 126 | 22.3 | 3.50 | 19.1 |
| 6 | 776 | 812 | 95.5 | 60.4 | 25.9 | 2.00 | 24.1 |
| 7 | 672 | 694 | 96.8 | 84.7 | 20.7 | 2.00 | 23.9 |
| 8 | 868 | 894 | 97.1 | 83.9 | 21.9 | 3.50 | 20.0 |
| 9 | 531 | 557 | 95.4 | 38.9 | 22.1 | 5.00 | 23.0 |
| 10 | 851 | 889 | 95.8 | 83.4 | 25.7 | 2.50 | 23.8 |
| 11 | 1242 | 1308 | 95.0 | 131 | 24.3 | 2.00 | 27.4 |
| 12 | 439 | 479 | 91.4 | 33.3 | 30.2 | 1.00 | 39.5 |
| 13 | 1107 | 1137 | 97.3 | 125 | 22.0 | 2.50 | 20.2 |
| 14 | 447 | 472 | 94.7 | 41.7 | 24.8 | 2.00 | 29.0 |
| 15 | 507 | 534 | 95.1 | 53.5 | 23.7 | 2.50 | 23.9 |
| 16 | 651 | 668 | 97.4 | 82.7 | 13.4 | 2.00 | 9.87 |
| 17 | 905 | 947 | 95.5 | 49.8 | 28.2 | 4.50 | 23.2 |
| 18 | 800 | 838 | 95.4 | 59.8 | 26.8 | 4.00 | 23.4 |
| 19 | 2811 | 3007 | 93.5 | 231 | 28.4 | 2.50 | 30.8 |
| 20 | 617 | 633 | 97.4 | 44.4 | 20.4 | 5.00 | 18.0 |
| 21 | 797 | 832 | 95.7 | 60.4 | 27.1 | 2.50 | 21.3 |
| 22 | 550 | 624 | 88.0 | 45.2 | 36.2 | 3.00 | 33.2 |
| 23 | 1040 | 1145 | 90.9 | 55.1 | 35.6 | 2.00 | 28.9 |
| 24 | 358 | 370 | 96.8 | 34.3 | 16.5 | 2.50 | 13.5 |
| Mean | 882 | 930 | 94.9 | 78.4 | 25.3 | 2.71 | 24.3 |
| SD | 511 | 543 | 2.6 | 46.0 | 5.5 | 1.03 | 6.7 |
| CV | 57.9 | 58.4 | 2.72 | 58.8 | 21.8 | 38.1 | 27.7 |

AUC: Area Under the concentration-in-blood curve
$C_{max}$: Concentration max
$T_{max}$: Time of the concentration max
MRT: Mean Residence Time
$t_{½}$: Half-time of the concentration max In Table 3, area ratios of the present invention to the traditional composition are listed, wherein the average is 1.10 and the maximum is 1.20. That is, the medicine of the present invention performs better bioavailability than the traditional medicine.

TABLE 3

| Subject No. | $AUC_{0 \rightarrow t}$ (hr × ng/mL) | $AUC_{0 \rightarrow \infty}$ (hr × ng/mL) | $C_{max}$ (ng/mL) |
|---|---|---|---|
| 1 | 1.60 | 1.63 | 1.79 |
| 2 | 2.07 | 1.99 | 1.83 |
| 3 | 0.349 | 0.350 | 0.275 |
| 4 | 0.857 | 0.877 | 1.04 |
| 5 | 2.37 | 2.31 | 2.52 |

TABLE 3-continued

| Subject No. | $AUC_{0 \to t}$ (hr × ng/mL) | $AUC_{0 \to \infty}$ (hr × ng/mL) | $C_{max}$ (ng/mL) |
|---|---|---|---|
| 6 | 1.17 | 1.16 | 1.15 |
| 7 | 0.832 | 0.839 | 1.08 |
| 8 | 0.724 | 0.719 | 0.730 |
| 9 | 0.426 | 0.433 | 0.389 |
| 10 | 1.31 | 1.33 | 1.67 |
| 11 | 1.03 | 1.02 | 1.06 |
| 12 | 0.582 | 0.605 | 0.397 |
| 13 | 1.28 | 1.25 | 1.48 |
| 14 | 1.24 | 1.19 | 1.71 |
| 15 | 0.761 | 0.778 | 0.796 |
| 16 | 0.868 | 0.880 | 1.14 |
| 17 | 0.547 | 0.556 | 0.405 |
| 18 | 2.59 | 2.44 | 3.52 |
| 19 | 0.942 | 0.932 | 1.36 |
| 20 | 0.938 | 0.945 | 0.771 |
| 21 | 0.639 | 0.573 | 0.689 |
| 22 | 0.943 | 0.992 | 0.993 |
| 23 | 0.993 | 1.05 | 0.430 |
| 24 | 1.29 | 1.27 | 1.66 |
| Mean | 1.10 | 1.09 | 1.20 |
| SD | 0.57 | 0.54 | 0.75 |

What is claimed is:

1. A high-bioavailability particle coated with fungicide and polymer, comprising:
   (a) a coating layer comprising 20~40 wt. % of itraconazole, 17~30 wt. % of poloxamer 407 polymer, 2~10 wt. % of acidic substance, 15~30 wt. % of talc, 2~6 wt. % of bonding agent, ethanol and dichloromethane based on the coating layer;
   (b) an anticoagulant layer comprising 50~70 wt. % of talc, 25~35 wt. % of hydroxypropyl methylcellulose (HPMC) and 1~10 wt. % of plasticizer based on the anticoagulant layer; and
   (c) a particulate core having a diameter 300~500 μm(30~50 mesh).

2. The high-bioavailability particle coated with fungicide and polymer of claim 1, wherein:
   the acidic substance of the coating layer mainly comprises citric acid.

3. The high-bioavailability particle coated with fungicide and polymer of claim 1, wherein:
   the bonding agent of the coating layer is hydroxypropyl methylcellulose (HPMC).

4. The high-bioavailability particle coated with fungicide and polymer of claim 1, wherein:
   the plasticizer of the anticoagulant layer is propylene glycol.

5. The high-bioavailability particle coated with fungicide and polymer of claim 1, which comprises 40~60 wt. % of the coating layer, 1~10 wt. % of the anticoagulant layer and 34~50 wt. % of the particulate core.

6. The high-bioavailability particle coated with fungicide and polymer of claim 1, which comprises about 51.37 wt. % of the coating layer, about 4.51 wt. % of the anticoagulant layer and about 44.12 wt. % of the particulate core.

* * * * *